US00PP33535P2

(12) United States Plant Patent
Mouton

(10) Patent No.: US PP33,535 P2
(45) Date of Patent: Oct. 5, 2021

(54) CLEMENTINE TREE NAMED 'EARLY ESBAL'

(50) Latin Name: ***Citrus* x *clementina***
Varietal Denomination: Early Esbal

(71) Applicant: Patrysberg Citrus (Pty) Ltd, Western Cape (ZA)

(72) Inventor: Schalk Mouton, Western Cape (ZA)

(73) Assignee: PATRYSBERG CITRUS (PTY) LTD, Western Cape (ZA)

( * ) Notice: Subject to any disclaimer, the term of this patent is extended or adjusted under 35 U.S.C. 154(b) by 0 days.

(21) Appl. No.: 16/974,313

(22) Filed: Dec. 22, 2020

(51) Int. Cl.
*A01H 5/08* (2018.01)
*A01H 6/78* (2018.01)

(52) U.S. Cl.
USPC ..... Plt./202

(58) Field of Classification Search
USPC ..... Plt./201, 202
See application file for complete search history.

*Primary Examiner* — Susan McCormick Ewoldt
(74) *Attorney, Agent, or Firm* — Michelle Bos Legal LLC

(57) ABSTRACT

A new clementine tree named 'Early Esbal' characterized by its early-maturing fruit.

6 Drawing Sheets

Latin name: *Citrus* x *clementina.*
Common name: Clementine.
Variety denomination: 'Early Esbal'.

BACKGROUND AND SUMMARY OF THE VARIETY

'Early Esbal' is a new clementine tree, originally discovered in a cultivated area near Citrusdal, WC, Republic of South Africa during the 2008/2009 growing season, as a spontaneous bud sport mutation of the 'Esbal' clementine variety (not patented). The 'Early Esbal' tree was first noticed because its fruit was coloring sooner than the fruit on surrounding 'Esbal' trees. Upon continued observation, the fruit was found to mature about 3 weeks earlier than 'Esbal'. The new variety was asexually propagated by grafting in 2011 at Citrusdal, Western Cape, Republic of South Africa, and has since been found to remain true to type over successive asexually propagated generations.

'Early Esbal' is distinguishable from parent variety 'Esbal' by its early maturity. 'Early Esbal' is distinguishable from similar variety 'Nules' (also known as 'Clemenules', not patented) by its early color development up to 2 weeks before 'Nules' and by its elongated fruit and the absence of parthenocarpy.

BRIEF DESCRIPTION OF THE PHOTOGRAPHS

The accompanying photographs were taken in 2019 and 2020 at Visalia, Calif. The trees depicted were topworked in 2018. The colors of the claimed variety may vary with lighting conditions. Color characteristics of the variety should therefore be determined with reference to the observations described herein, rather than from these illustrations alone.

DETAILED BOTANICAL DESCRIPTION

Figure 1:
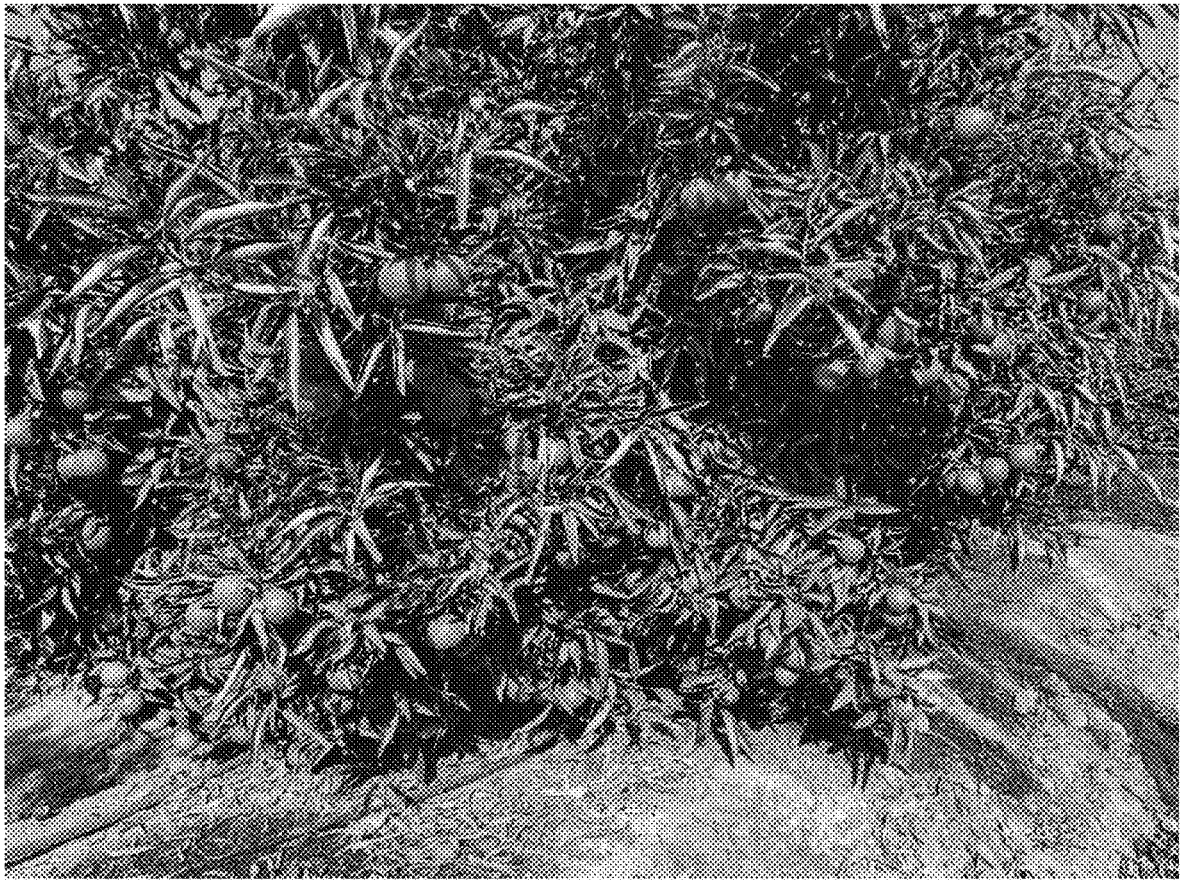
FIG. 1 shows an 'Early Esbal' clementine tree.
Figure 2:
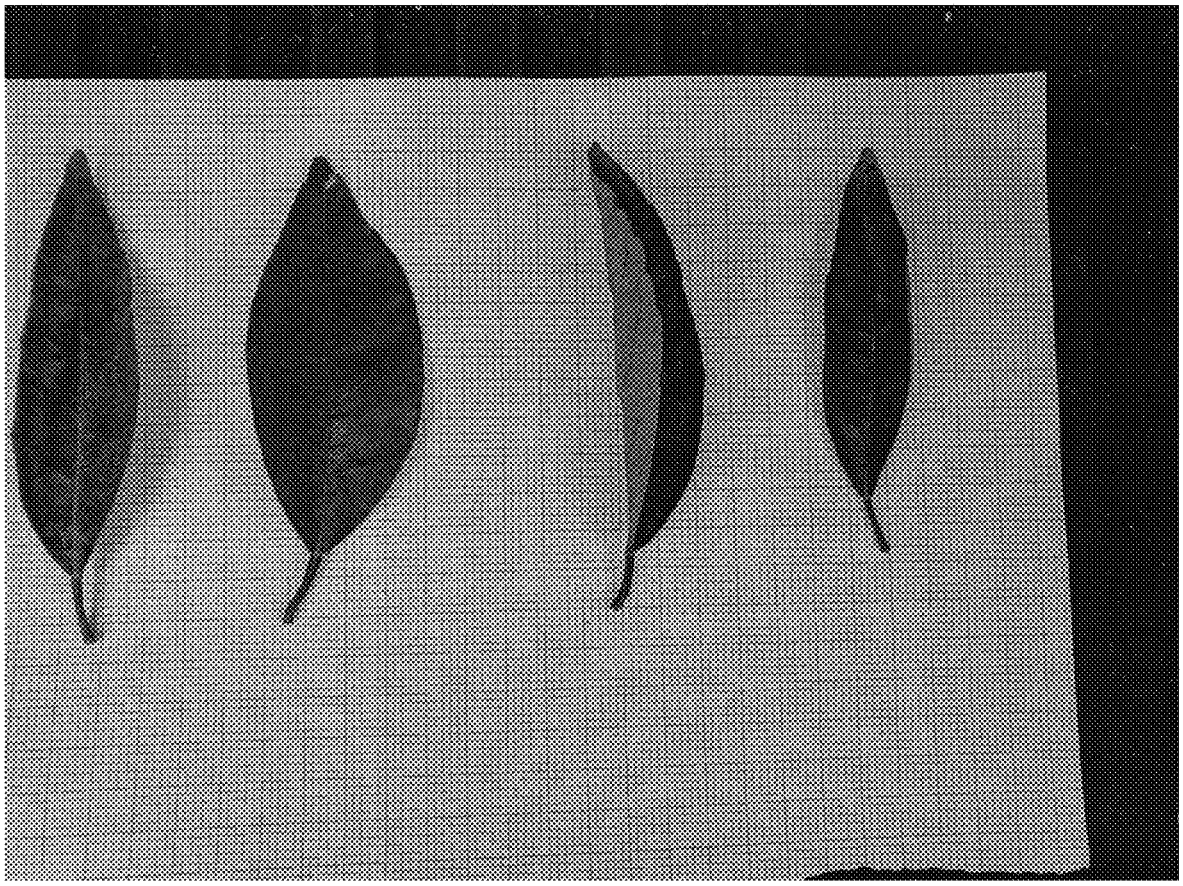
FIG. 2 shows 'Early Esbal' leaves.
Figure 3:
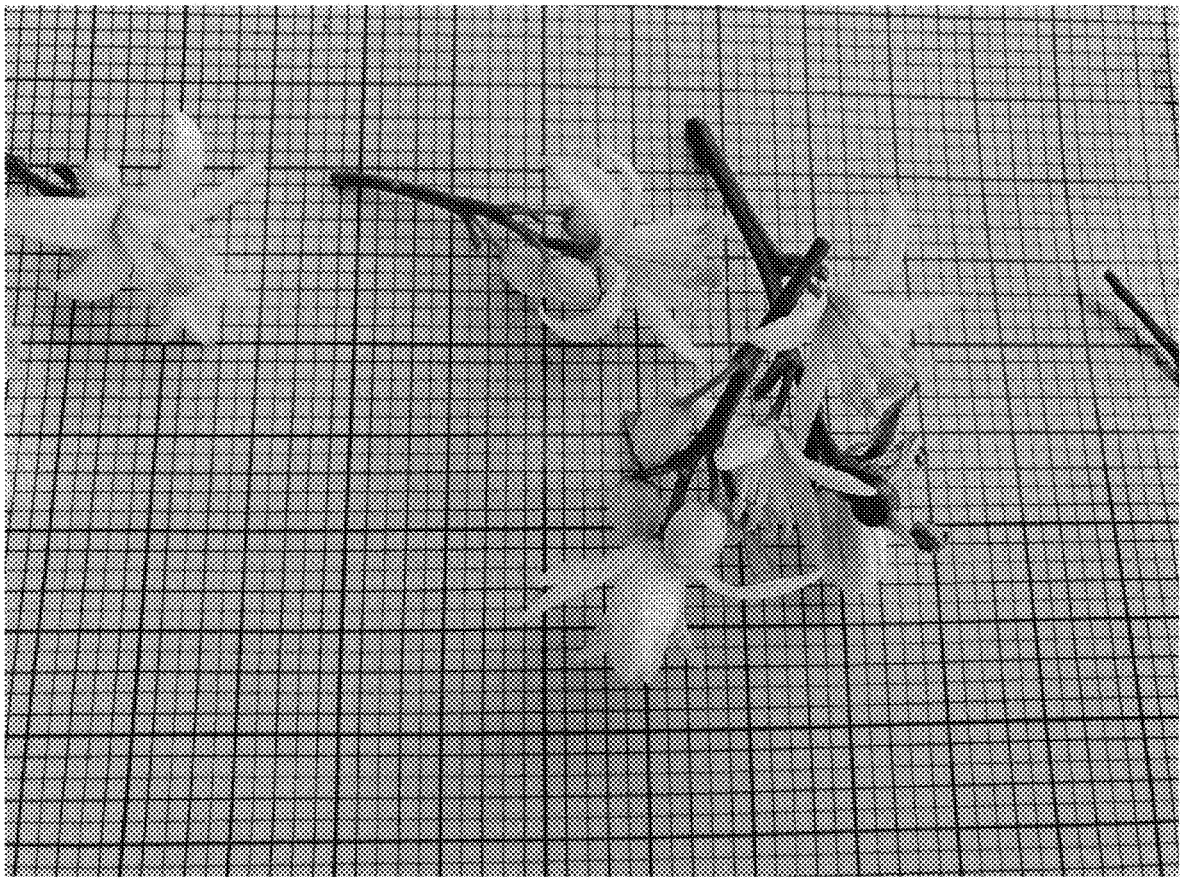
FIG. 3 shows buds and blossoms from an 'Early Esbal' tree.
Figure 4:
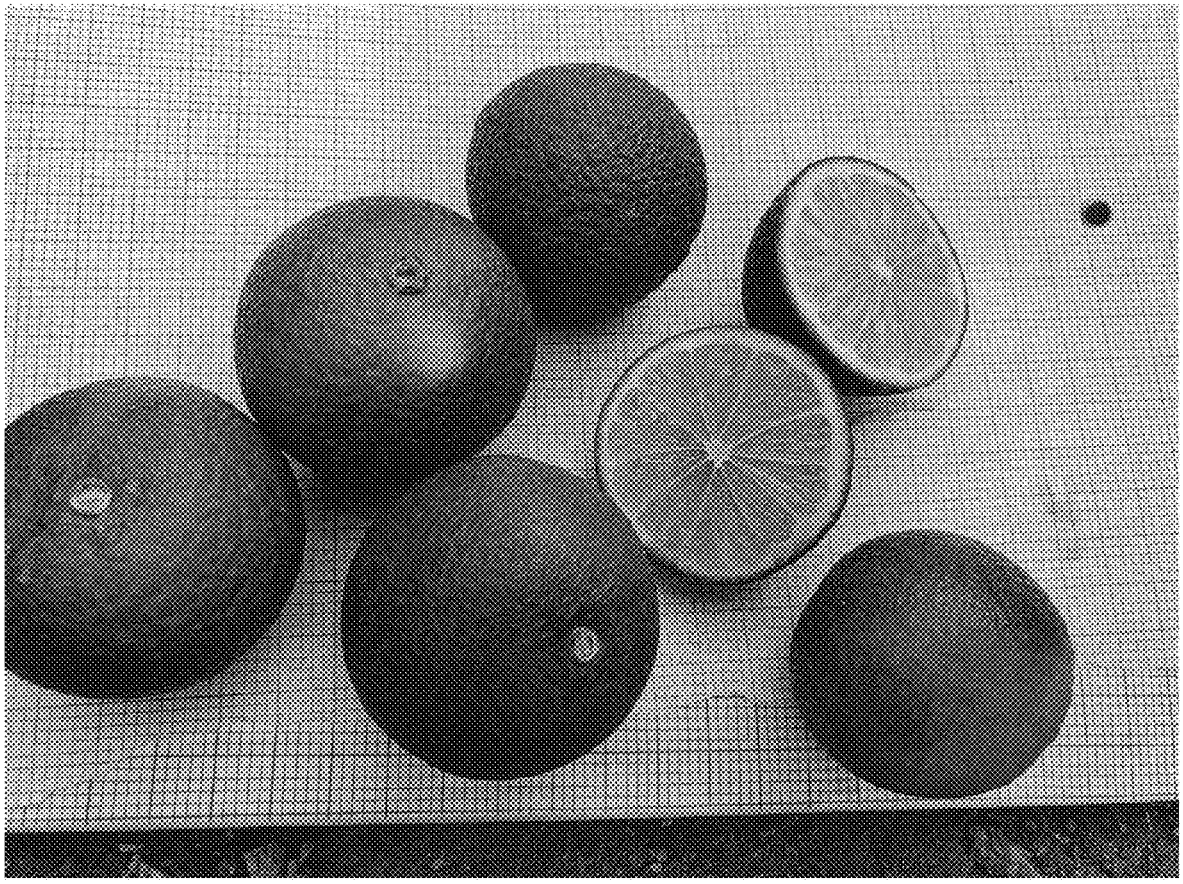
FIG. 4 shows whole and sectioned 'Early Esbal' fruit.
Figure 5:
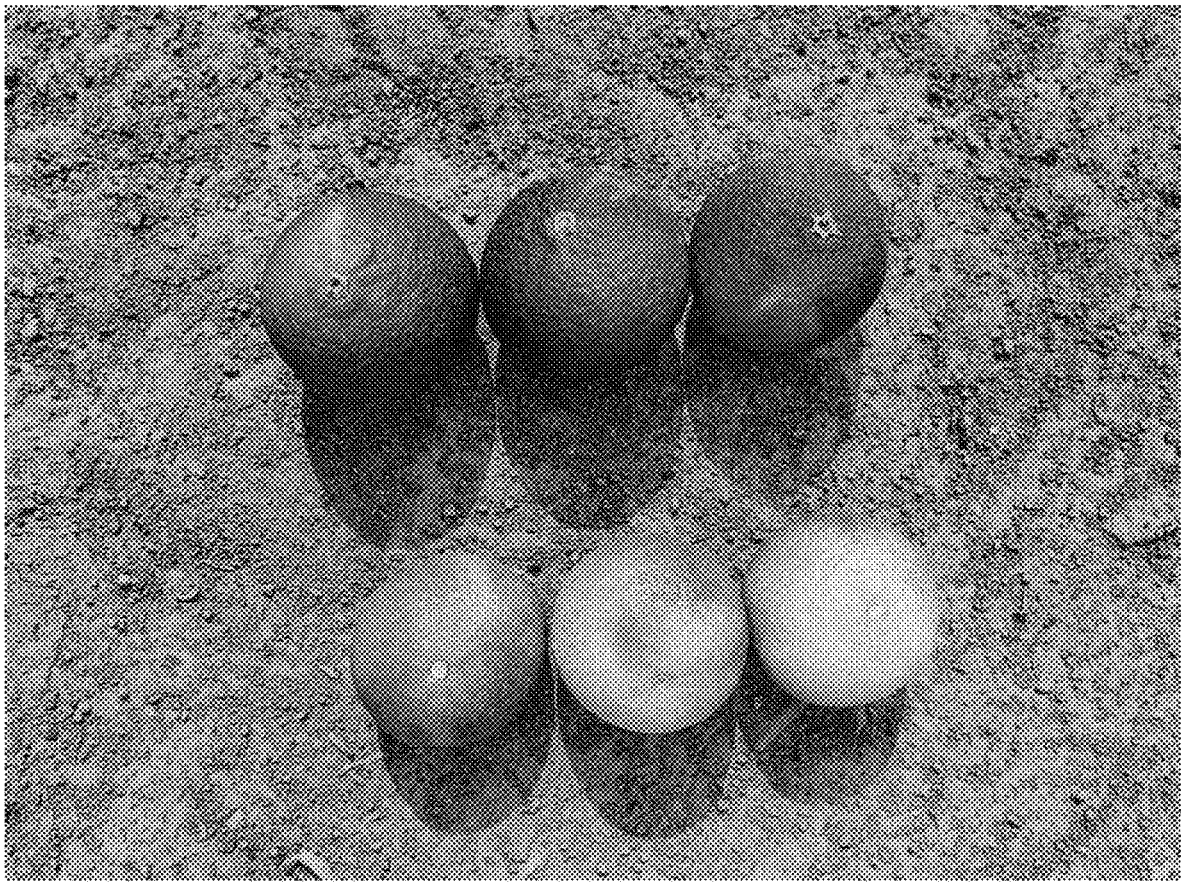
FIG. 5 shows 'Nules' fruit (top) and 'Early Esbal' fruit (bottom)
Figure 6:
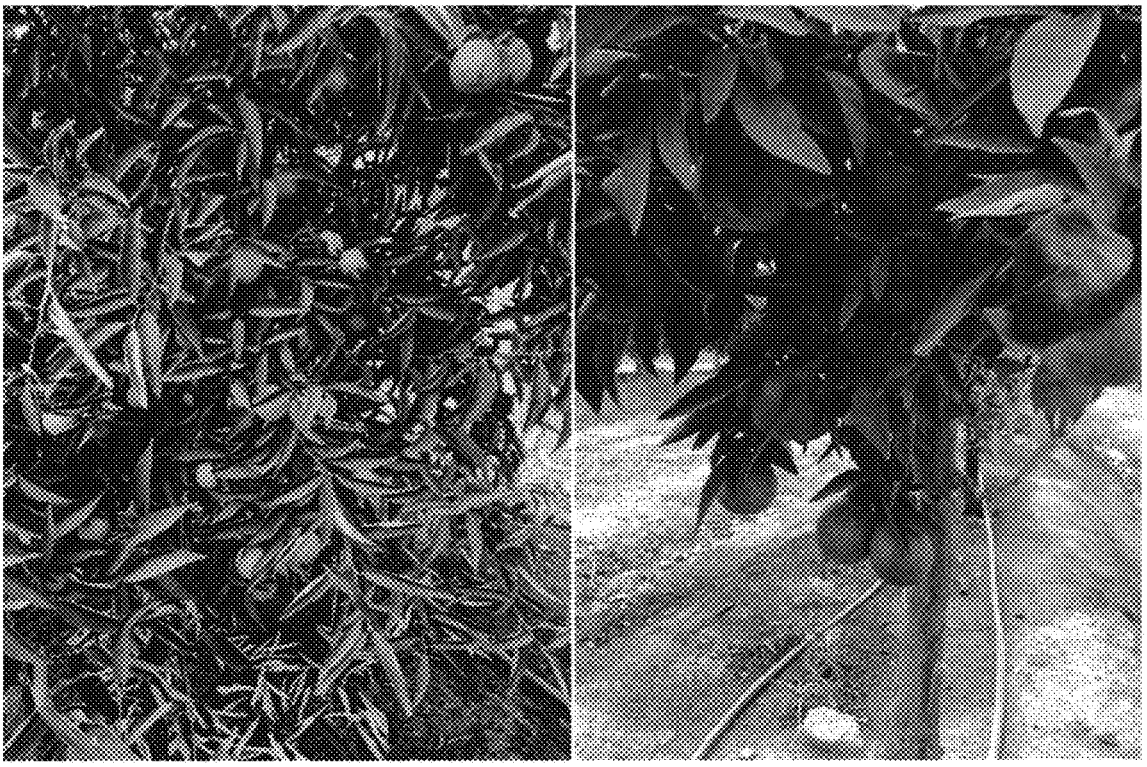
FIG. 6 shows photos taken the same day of fully colored 'Early Esbal' fruit (left) and 'Nules' fruit (right).

The following detailed botanical description is based on observations recorded at Visalia, Calif. in 2019 and 2020. The trees described were topworked in 2018 onto 'Carrizo' rootstock (not patented). The characteristics described will vary somewhat depending upon cultural practices, climatic conditions, location and growing season. Quantified measurements are expressed as an average of measurements taken from a number of individual plants of the claimed variety. The measurements of any individual plant or any group of plants of the variety may vary from the stated average. Colors are described with reference to The Royal Horticultural Society Colour Chart (5th Ed., v.2).

DETAILED BOTANICAL DESCRIPTION

Tree:
- *Vigor.*—Medium.
- *Density of canopy.*—Medium.
- *Habit.*—Upright.
- *Height.*—150 cm to 190 cm.
- *Spread.*—110 cm to 140 cm.
- *Trunk diameter* (*at* 30 *cm above the graft*).—4.5 cm to 4.75 cm.
- *Bark texture.*—Smooth.
- *Bark color.*—Grey-brown 199D.
- *Tendency toward alternate bearing.*—None.
- *Chilling requirement.*—None.

Branch:
- *Length.*—76 cm.
- *Diameter.*—1 cm.
- *Crotch angle.*—Narrow to medium.
- *Bark color.*—Young wood yellow-green 144B; mature wood grey-brown 199D.
- *Bark texture.*—Smooth.

*Thorns*.—Very few to none.
*Current year shoot length*.—10 cm.
*Current year shoot color*.—Yellow-green 149B.

Flowers:
*Bud shape*.—Pyriform.
*Bud length*.—0.5 cm to 1.25 cm.
*Bud diameter*.—0.5 cm to 0.5 cm.
*Bud color*.—White NN155B.
*Quantity of blossoms per cluster*.—3 to 5.
*Relative position of petal margins*.—Not touching.
*Blossom diameter*.—2.7 cm.
*Blossom depth*.—0.5 cm.
*Pollen*.—Yellow 8C.
*Sepal length*.—3 mm.
*Sepal width*.—1.5 mm to 2 mm.
*Sepal shape*.—Acuminate.
*Sepal margin*.—Entire.
*Sepal color—upper surface*.—Yellow-green 150C.
*Sepal color—lower surface*.—Yellow-green 150C.
*Quantity of petals per flower*.—5.
*Petal shape*.—Lanceolate.
*Petal apex*.—Acute.
*Petal margin*.—Entire.
*Petal length*.—1.0 cm to 1.25 cm.
*Petal width*.—0.5 cm to 0.6 cm.
*Petal color—upper surface*.—White NN155B.
*Petal color—lower surface*.—White NN155A.
*Pedicel length*.—0.7 cm.
*Pedicel diameter*.—1 mm to 2 mm.
*Pedicel color*.—Yellow-green N144B.
*Pistil quantity per flower*.—14 to 15.
*Pistil length*.—0.9 cm to 1.2 cm.
*Pistil color*.—Yellow-green 145C.
*Stigma length*.—2 mm.
*Stigma color*.—Yellow-green 153D.
*Style length*.—0.8 cm to 1.0 cm.
*Style color*.—White NN155B.
*Ovary length*.—4 mm.
*Ovary diameter*.—3.5 mm.
*Ovary color*.—Green 143B.
*Anther quantity per flower*.—14 to 15.
*Anther length*.—2.0 to 2.5.
*Anther color*.—Yellow-green 154B.
*Date of first bloom*.—April 10 (2020 growing season).
*Date of full bloom*.—April 20 (2020 growing season).
*Date of first fruitlet fall*.—May 15 (2020 growing season).
*Pollenizer*.—Not required.

Leaves:
*Length*.—9 cm to 11 cm.
*Width*.—4.0 cm to 4.75 cm.
*Length/width ratio*.—About 2.25:1.
*Blade margin*.—Entire.
*Leaf shape*.—Elliptic.
*Apex shape*.—Acute.
*Base shape*.—Cuneate, aequilateral.
*Venation*.—Pinnate.
*Arrangement*.—Alternate.
*Color of upper surface*.—Green 143A.
*Color of lower surface*.—Yellow-green N144B.
*Vein color*.—Green 143C.
*Petiole length*.—1.5 cm to 2.0 cm.
*Petiole diameter*.—2.5 mm.
*Petiole color*.—Green 143A.
*Wings*.—Not present.

Fruit:
*Quantity per cluster*.—3.
*Axial diameter*.—5.2 cm.
*Apical diameter*.—4.5 cm.
*Weight*.—60 to 65 g.
*General shape in profile*.—Round.
*Position of maximum diameter*.—Equator.
*Navel*.—Present.
*Rind color*.—Orange 28B.
*Oil gland diameter*.—1.0 mm to 1.5 mm.
*Oil gland density*.—4 to 6 per $cm^2$.
*Rind thickness*.—2 mm.
*Ease of peeling*.—Easy.
*Rind texture*.—Smooth to somewhat pebbly.
*Albedo thickness*.—1.5 mm.
*Quantity of fruit segments per fruit*.—10.
*Toughness of segment membrane*.—Soft.
*Segment length*.—3.8 cm.
*Segment diameter*.—2.0 cm.
*Juice sac length*.—9 mm to 11 mm.
*Juice sac shape*.—Elongated.
*Juice sac color*.—Orange 23B.
*Juice soluble solids*.—10.1° Brix.
*Relative harvest maturity*.—Early.
*Harvest begins*.—Mid- to late October.
*Seeds*.—None (trees netted during flowering).
*Stem length*.—5 mm.
*Stem diameter*.—3 mm.
*Stem color*.—Yellow-green N144B.
*Harvest yield*.—35 to 50 metric tons/hectare.
*Market use*.—Fresh, domestic and export.
*Keeping quality*.—Good.
*Pest and disease resistance*.—None noted.
*Pest and disease susceptibility*.—None noted.
*Winter hardiness*.—Unknown.
*Drought and heat tolerance*.—Unknown.

I claim:

1. A new and distinct variety of clementine tree substantially as described and illustrated herein.

* * * * *